United States Patent
Kiy

(10) Patent No.: US 6,716,617 B1
(45) Date of Patent: Apr. 6, 2004

(54) FERMENTATION METHOD WITH CONTINUOUS MASS CULTIVATION OF CILIATES (PROTOZOA) FOR PRODUCING BIOGENOUS VALUABLE SUBSTANCES

(75) Inventor: Thomas Kiy, Frankfurt (DE)

(73) Assignee: Nutrinova (DE)

( * ) Notice: Subject to any disclaimer, the term of this patent is extended or adjusted under 35 U.S.C. 154(b) by 0 days.

(21) Appl. No.: 09/508,977

(22) PCT Filed: Sep. 10, 1998

(86) PCT No.: PCT/EP98/05770

§ 371 (c)(1),
(2), (4) Date: Mar. 17, 2000

(87) PCT Pub. No.: WO99/15634

PCT Pub. Date: Apr. 1, 1999

(30) Foreign Application Priority Data

Sep. 19, 1997 (DE) .......................................... 197 41 489

(51) Int. Cl.⁷ ................................................. C12N 1/10
(52) U.S. Cl. .................... 435/258.1; 435/244; 435/947; 424/780
(58) Field of Search .............................. 435/258.1, 244, 435/947; 424/780

(56) References Cited

U.S. PATENT DOCUMENTS 6,143,539 A * 11/2000 Kiy ............................ 435/194

FOREIGN PATENT DOCUMENTS

DE 4238842 * 5/1994
FR 2334630 7/1977

OTHER PUBLICATIONS

Stafford Iln Demain et al., Industrial Microbiology and Biotechnology, 1986, ASM, pp. 144–145.*
Curds et al., J. Gen Microbiol. (1968) 54(3), 343–358.*
Trager, W., et al, Science 193:673–675, "Human malaria parasites in continuous culture", XP–002090949 (1976).
Rosenbaum, N., et al, Chem. Abs. 66:17297, "Induction of a phospholipid requirement and morphological abnormailites in Tetrahymena pyriformis by growth . . . ", XP–002090950 (1967).
Yamin, M. A., et al, Chem. Abs. 94:61384, "Cellulose metabolism by the flagellate Trichonympha from a termite is independent of endosymbiotic bacteria", XP–002090951 (1981).
Van Wagtendonk, W. J., et al, Chem. Abs. 76 :43778, "Axenic cultivation of Paramecium aurelia", XP–002090952 (1972).
Orbit Derwent English Abstract of FR 2,334,630 (AN–1977–41661Y) (Jul. 8, 1977).
Orbit Derwent English Abstract of DE 4,238,842 (AN—1994–168701) (May 19, 1994).

* cited by examiner

*Primary Examiner*—Irene Marx

(57) ABSTRACT

In the fermentation process according to the invention with continuous mass cultivation of ciliates (protozoa), the ciliate cells are cultivated in a complex axenic medium—free from living feed or prey organisms—and the biomass containing the desired biogenous valuable substances is obtained by continuous (permanent) cell extraction.

22 Claims, 3 Drawing Sheets

Figure 1:
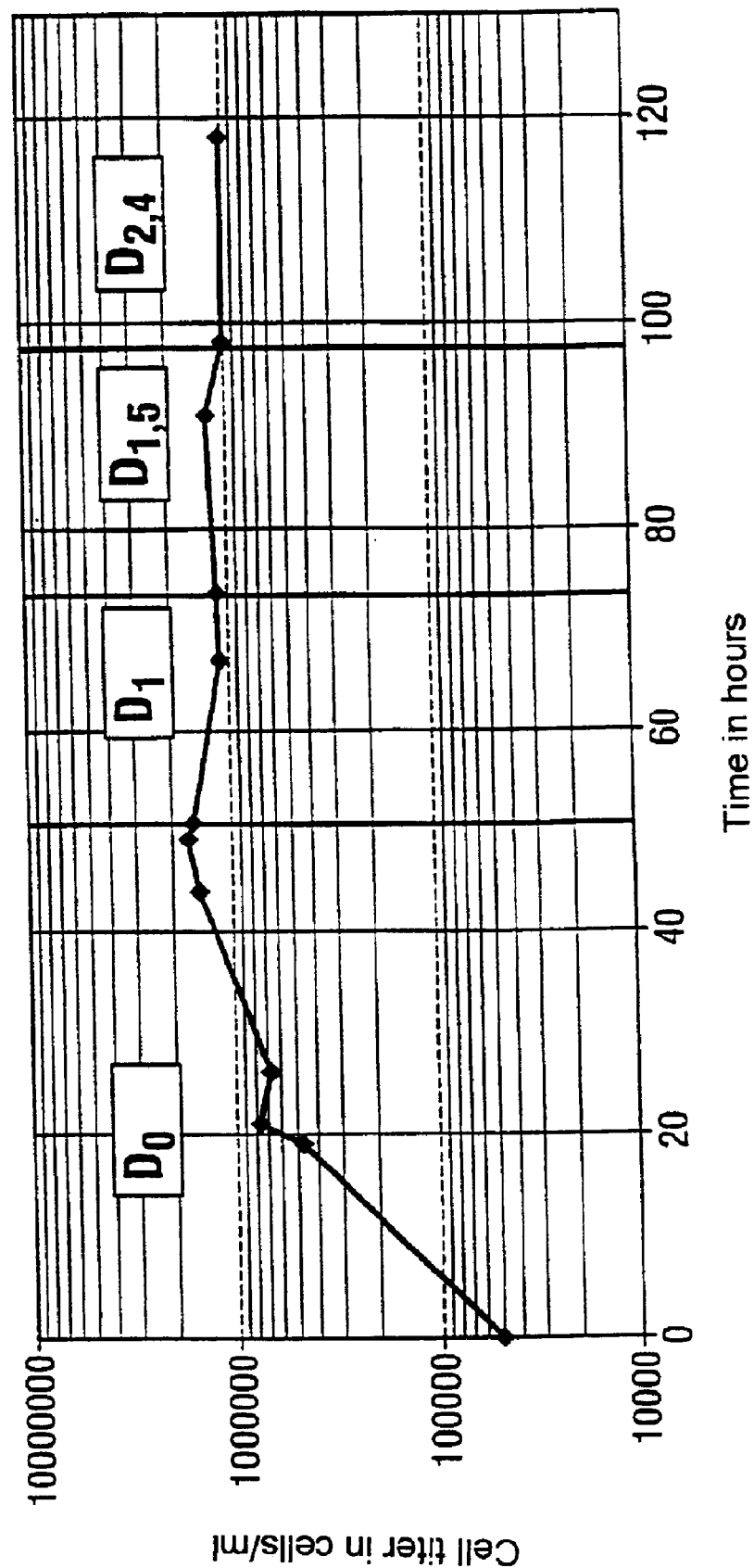

FERMENTATION METHOD WITH CONTINUOUS MASS CULTIVATION OF CILIATES (PROTOZOA) FOR PRODUCING BIOGENOUS VALUABLE SUBSTANCES

The invention relates to a fermentation process with continuous mass cultivation of ciliates (protozoa) for producing biogenous valuable substances, where the biomass containing the desired biogenous valuable substances is obtained by continuous (permanent) cell extraction.

To date, only initial attempts have been made in the biotechnological utilization of ciliates—a class of protozoa—, although a large number of metabolites of these organisms are of economical interest, for example lysosomal enzymes. As yet, only few biotechnological processes for obtaining biogenous valuable substances from ciliates have been described, —mainly for the ciliate Tetrahymena (Kiy & Tiedtke, 1991, Appl. Microbiol. Biotechnol., 35, 14; Kiy et al., 1996, Enzyme Microb. Technol., 18, 268; Kiy & Tiedtke, 1992, Appl. Microbiol. Biotechnol., 38, 141), —and these are exclusively processes for obtaining excreted cell products, i.e. those cell products which are given off by the ciliate cells into the culture medium. In this kind of process, the ciliates are cultivated in fermenters and the culture medium containing the excreted biogenous valuable substances is removed periodically, in more or less regular intervals, and exchanged for fresh medium. During the exchange of the medium, the ciliates are retained in the fermenter using certain methods—for example the use of membranes, cell immobilization and the like—, so that virtually no cell material is lost and the cell culture exists in principle permanently. However, to obtain biogenous valuable substances which are attached to the cell it is necessary to harvest the total of the cells, the so-called biomass. To this end, in general—i.e. in the generally known fermentation processes with bacteria or fungi as producers of valuable substances—a so-called batch fermentation is carried out, where the fermenter is seeded and the cells are cultivated until the maximum biomass or product concentration has been reached. The biomass is then harvested. Such processes have already been described for various ciliates such as Paramecium, Colpoda and Tetrahymena (Proper & Garver, 1966, Biotechnol. Bioeng., 8, 287, Schönefeld et al., 1986, J. Protozool., 33, 222; Kiy & Tiedtke, 1992, Appl. Microbiol. Biotechnol. 37, 576).

However, batch fermentation processes have the fundamental disadvantage that, at intervals, cleaning, re-seeding of the fermenter and an intensive monitoring and looking after of the cell culture is required—in particular during the critical growth phase.

From the fermentation technique with bacteria or yeasts as producers of valuable substances, in addition to the bath fermentation process, the "continuous fermentation process" is also known. In this process, the cells are cultivated in the fermenter until they have reached a certain cell density and then permanently harvested by continuous cell extraction from the fermenter, while at the same time fresh culture medium is added to the same extent. The amount of cells extracted per time unit (the cell extract) is such that the cells which remain in the fermenter can easily recompensate the reduction of the cell density due to the harvest, by continuous cell divisions. In the range if a certain cell extraction rate or dilution rate "D", the cell density in the fermenter thus remains constant, although culture and accordingly the desired product are harvested continuously.

In principle, this continuous fermentation process is economically far superior to batch fermentation; however, its realization requires that the cultivated or bred organisms grow and multiply relatively quickly and uniformly, and that they are insensitive to the stirring and shear forces which are encountered in a continuous fermentation process.

Of ciliates, however, it is generally known that frequently they grow and multiply only very slowly, that they pass through different growth phases and that they react very sensitively to stirring and shear forces (Curds & Cockburn, 1971, Journal of General Microbiology 66, 95–109; Middler & Finn, 1966, Biotechnology and Bioengineering 8, 71–84). Attempted continuous mass cultivations of ciliates have indeed been described, but exclusively with the use of bacteria-containing culture media and with resulting maximum cell densities of a few ten thousand cells per ml, despite a cultivation of 10 days or more (Curds & Cockburn, supra.). For use on an industrial scale, such cell densities are totally insufficient. In addition, the cultivation described by Curds & Cockburn is therefore also completely unsuitable for industrial use because it prescribes the use of a medium containing prey organisms, i.e. bacteria. In a bacteria-containing culture medium, the bacteria do, of course, also multiply permanently, the extent depending on how many ciliates are present. The coexistence equilibrium of ciliate population and bacteria population is very labile, and even a slight intervention can cause substantial changes in both populations.

Furthermore, the experiments of Curds & Cockburn were carried out more than 25 years, ago, and they have apparently confirmed the opinion of those skilled in the art that ciliates are unsuitable for a continuous fermentation process on an industrial scale.

It is an object of the present invention to provide a process for continuous fermentation of ciliates with cell extraction, which avoids the abovementioned disadvantages and is very suitable, in particular, for industrial use.

This object is achieved by a process of the type mentioned at the outset, where the ciliate cells are cultivated in a complex axenic medium.

For the purpose of this invention, a complex medium is a nutrient medium in aqueous solution of natural products or extracts obtained therefrom for cultivating microorganisms.

For the purpose of this invention, axenic medium is a nutrient medium which is free of feed and prey organisms (so-called food organisms).

The process according to the invention is based on the surprising finding that a continuous fermentation process with cell extraction using complex axenic media can also be carried out successfully and in an economically highly rewarding manner using pure ciliate cultures. Continuous cell densities in an order of magnitude of 1 million cells per ml can be realized without any problems, in the case of Tetrahymena as early as from the third day after the beginning of the cultivation. Thus, the prejudice of those skilled in the art that ciliates are unsuitable for continuous mass cultivation with cell densities of several hundred thousand to millions of cells per ml using known fermenters and in the presence of the shear forces which are usually encountered, in axenic medium—i.e. without living feed or prey organisms, is overcome since:

they grow too slowly and not uniformly enough,
they show only little resistance to stirring and shear forces and are very easily and rapidly damaged and/or destroyed by such forces, and
in the cultivation attempts that have been carried out so far, in spite of a prey-organism-containing media being used, and thus a substantially natural diet, only relatively very low maximum cell densities have been reached.

Using the process according to the invention, it is possible for the first time to employ ciliates for the industrial production of biogenous valuable substances attached to the cell, and thus to obtain, on an economically important scale, in particular those valuable substances which are only known from ciliates, such as, for example, taurolipids and tetrahymanol, or those which are produced extensively specifically by ciliates, such as, for example, gamma-linolenic acid, docosahexaenoic acid, eicosapentaenoic acid, octatetraenoic acid and arachidonic acid.

Since the ciliates are kept as a pure culture—i.e. free from other living organisms—, important disturbing factors are avoided a priori, and even the technical expense is limited to a minimum: fermenters for regrowing the prey organisms, for example, are completely redundant.

The products which can be obtained from the extracted biomass include peptides and proteins, especially enzymes (for example β-hexosaminidase, L-asparaginase, diisopropylfluorophosphatase, glucosidase, fucosidase, phosphatase, nuclease or cathepepsin.L), fatty acids and lipids (for example gamma-linolenic acid, docosahexaenoic acid, eicosapentaenoic acid, octatetraenoic acid, arachidonic acid, phosphonolipids, taurolipids or tetrahymanol), polysaccharides, nucleic acids, secondary metabolites, polymers, etc. It is also possible for the biomass as such to be the product.

The group of the ciliates which can be cultivated by the process described includes all taxonomic ciliate sub-groups which can be cultivated in principle in conventional standing and/or shaking cultures or batch fermentations on axenic nutrient media or nutrient media which comprise, as nutrient, the killed biomass of a feed organism. These are, in particular, the ciliate sub-classes Holotricha, Peritricha, Spirotricha and Suctoria, and very particularly the orders Tetrahymena, Paramecium, Colpoda, Glaucoma, Parauronema, Engelmanniella, Stylonichia, Euplotes and Colpidium (classification according to K. Hausmann: Protozoologie, Thieme Verlag, 1985). Furthermore, the invention is not limited to wild strains but includes mutants and recombinant strains.

In a preferred embodiment of the process according to the invention, the fermentation is carried out in a stirred or bubble column or airlift fermenter.

During the fermentation, the pH can be regulated, preferably to a value in the range from pH 4 to pH 9. Depending on the ciliate species, the fermentation temperature is between 15 and 40° C.

As carbon source, preferably at least one of the substances listed below is used, i.e.: glucose, fructose, xylose, sucrose, maltose, starch, fucose, glucosamine, lactose, molasses, dextran, fatty acids (for example oleic acid), soya oil, sunflower oil, glycerol, glutamic acid, mannitol, skim-milk powder or acetate.

The concentration of the carbon source should be between 0.2 and 20% by weight, based on the culture medium.

As nitrogen source, preferably at least one of the substances listed below is used, i.e.: peptones, yeast extract, malt extract, meat extract, skim-milk powder, casamino acid, corn steep liquor, organic nitrogen sources, such as Na-glutamate and urea, inorganic nitrogen sources, such as ammonium acetate, ammonium sulfate, ammonium chloride or ammonium nitrate.

The concentration of the nitrogen source should be between 0.1 and 10% by weight, based on the culture medium.

In a variant of the process according to the invention, at least one phosphate source, for example potassium phosphate or potassium dihydrogen phosphate, is added to the culture medium. Alternatively or cumulatively, it is also possible to add ammonium sulfate, sodium sulfate, magnesium, iron, copper, calcium, vitamins, trace elements and growth factors, to further optimize the growth and multiplication rate of the ciliate culture in question.

The continuously harvested biomass is preferably separated off from the culture medium using centrifugation, tangential filtration, microfiltration, sedimentation, flotation or separators. However, other methods are also feasible.

In a preferred embodiment of the process according to the invention, the cell extraction rate or dilution rate D (=volume exchanged per day/operating volume of the fermenter) is in the range from 0.1 to 12 (=1/10 to 12/1), depending on the growth rate of the ciliate strain. Below, the invention is illustrated in more detail using working examples.

EXAMPLE 1

Continuous Fermentation of Tetrahymena Pyriformis

Tetrahymena pyriformis was cultivated in a 2 l fermenter of the Biostat MD type (Braun Biotech, Melsungen), under the following conditions:

Medium:

Water with additives of 0.5% by weight of Proteose Peptone 0.1% by weight of yeast extract 3% by weight of liquid starch sugar 1 ml/l of iron trace Fermentation conditions:

Temperature: 30° C.

Oxygen saturation: 20% pH regulation: pH 7

Start ($t_{0\ h}$): inoculum 50,000 cells/ml; cultivation by the batch process type Beginning of the continuous fermentation: $t_{51\ h}$ with D=1;

Continuation of the continuous fermentation: from $t_{78\ h}$ with D=1.5; from $t_{98\ h}$ with D=2.4

At the beginning of the cultivation, the medium was inoculated with about 50,000 cells, and this starter culture was cultivated by a batch process until the cell population was at the end of the multiplication phase and just before entering the stationary phase. At this time—in the present example 51 hours after inoculation ($t_{51\ h}$)—, the fermentation was changed to continuous fermentation, i.e. from then on cell-containing medium was continuously withdrawn, and the corresponding amount of cell-free medium was added. At the beginning of the continuous fermentation, the cell extraction or dilution rate (=amount by volume of medium exchange per day per operating volume of the fermenter) was D=1, i.e. per day, the entire content of the fermenter (2 l) was exchanged once, and 2 l of ciliate-containing medium were obtained. This medium contained about 1 million cells per ml.

27 hours after the beginning of the continuous fermentation (=78 hours after the inoculation=$t_{78\ h}$), the cell extraction rate or dilution rate was increased to D=1.5, i.e. from this point of time onwards, about 3 l of ciliate-containing medium were obtained per day. The cell density was virtually unchanged at about 1 million cells per mi. After a further 20 hours (=98 hours after the inoculation=$t_{98\ h}$), the cell extraction rate or dilution rate was increased once more, to D=2.4, i.e. about 5 l of ciliate-containing medium were obtained per day, the cell density being, as before, virtually unchanged at about 1 million cells/ml.

The results of this fermentation process are shown diagrammatically in FIG. 1. From the plot shown therein, it is evident that, although cells were continuously extracted, there was no dilution, but a permanent and continuous multiplication of the ciliates. In other words: even at a relatively large cell extraction (D=2.4), the culture was always in a dynamic equilibrium between cell extraction and cell multiplication.

EXAMPLE 2

Continuous Fermentation of Tetrahymena Thermophila

Tetrahymena thermophila was cultivated in a 2 l fermenter of the Biostat MD type (Braun Biotech, Melsungen), under the following conditions:

Medium:
Water with additives of
5 g/l of Proteose Peptone
1 g/l of yeast extract
1 ml/l of iron trace
1% by weight of glucose in the form of liquid starch sugar
Fermentation conditions:
Temperature: 30° C.
Oxygen saturation: 20%
pH regulation: pH 7
Start ($t_{0\ h}$): inoculum 50,000 cells/ml; cultivation by the batch process type
Beginning of the continuous fermentation: 45 h with D=1.2;
Continuation of the continuous fermentation: from $t_{178\ h}$ with D=2.4;
from $t_{198\ h}$ with D=3

The process was carried out in principle as described under EXAMPLE 1.

Figure 2:
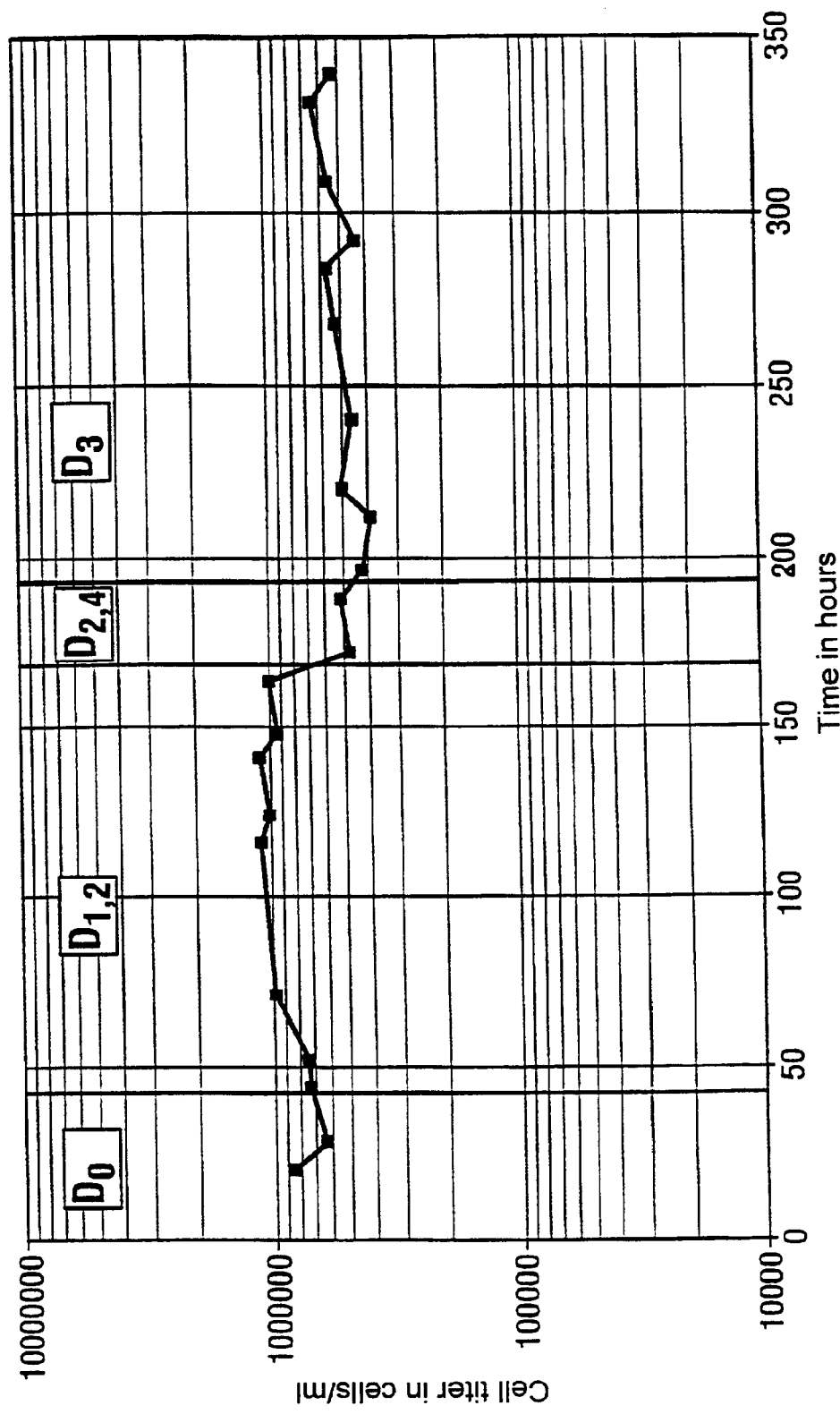

In FIG. 2, the growth or multiplication behavior of the ciliate population under the fermentation conditions mentioned is shown diagrammatically. From the plot shown, it is evident that the increase of the cell extraction or dilution rate from D=1.2 to D=2.4 (duplication) resulted in a reduction of the cell density from about 1 million cells/ml to about 500,000 cells/ml (halving), but that this cell density then remained relatively constant and did not decrease any further, even when the cell extraction or dilution rate was increased further from D=2.4 to D=3.

EXAMPLE 3

Continuous Fermentation of Tetrahymena Thermophila

Medium:
Water with additives of
20 g/l of skim-milk powder
10 g/l of glucose
5 g/l of yeast extract
1 ml/l of iron trace
Fermentation conditions:
Temperature: 30° C.
Oxygen saturation: 20%
Stirrer: as 2. Cascade for oxygen regulation
pH regulation: pH 7

Start ($t_{0\ h}$): inoculum 50,000 cells/ml; cultivation by the batch process type
Beginning of the continuous fermentation: $t_{20\ h}$ with D=1.125;
Continuation of the continuous fermentation
from $t_{68\ h}$ with D=1.9;
from $t_{139\ h}$ with D=4.14;
from $t_{168\ h}$ with D=4.94

The process was in principle carried out as described under EXAMPLE 1.

Figure 3:
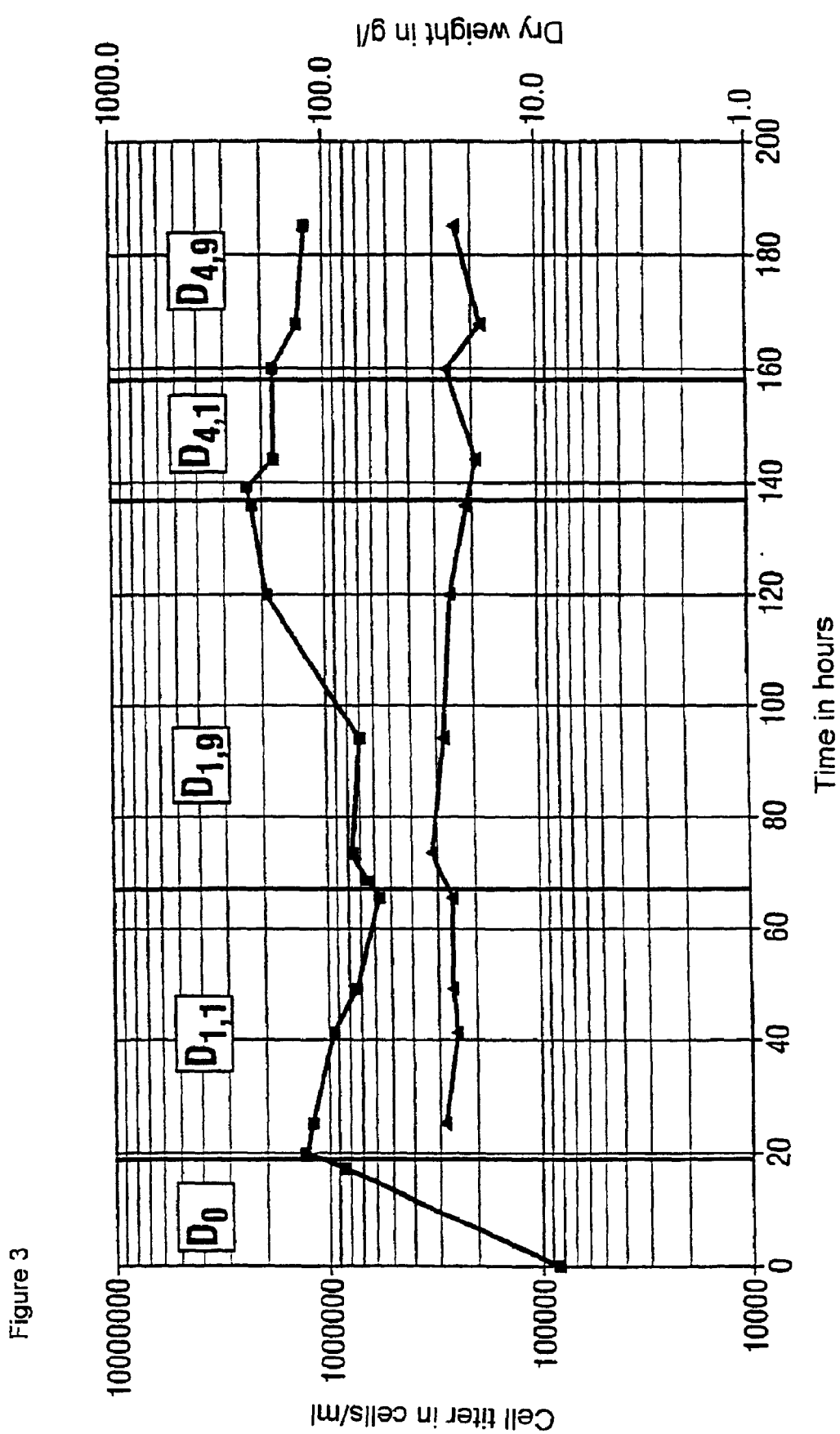

In FIG. 3, the growth or multiplication behavior of the ciliate population under the fermentation conditions mentioned above is shown diagrammatically. The plot shown indicates that, at the beginning of the continuous fermentation, the cell density decreased from initially about 1 million cells per ml to about 600,000 cells per ml. However, in spite of the cell extraction or dilution rate being increased, the cell population recovered within 1.5 days (about 36 hours) and, after about 4 days (90 hours) after the beginning of the continuous fermentation, had once more reached its initial density of 1 million cells per ml. Even when the cell extraction or dilution rate was increased further to D=4.1 and finally to D=4.9, the actual value was never again beneath this value.

The lower plot in FIG. 3 shows the results of determinations of the dry weight of the cells (in g per l) during the duration of the cultivation. The plot, which is essentially parallel to the curve for cell multiplication, shows that cell multiplication does not take place at the expense of the cell size or the cell volume of the individual ciliate cells, but that more biomass is indeed produced.

EXAMPLE 4

Continuous Fermentation of Colpidium Campylum

Colpidium campylum was cultivated in a 2 l fermenter of the Biostat MD type (Braun Biotech. Melsungen) under the following conditions:

Medium:
Water with additions of
20 g/l skim-milk powder
10 g/l of glucose
5 g/l of yeast extract
1 ml/l of iron trace
Fermentation conditions:
Temperature: 25° C.
Oxygen saturation: 20%
Stirrer: 108 rpm
pH regulation: pH 7
Start ($t_{0\ h}$): inoculum 50,000 cells/ml; cultivation by the batch process type
Beginning of the continuous fermentation: $t_{114.75\ h}$ with D=0.665;
Continuation of the continuous fermentation
from $t_{140\ h}$ with D=0.632
from $t_{159\ h}$ with D=0.462

The process was carried out in principle as described under EXAMPLE 1.

What is claimed is:

1. A continuous fermentation process for the production of a biomass of ciliate cells containing a biogenous substance, comprising:
   (i) continuously cultivating ciliates in a volume of complex axenic aqueous culture medium to produce a biomass of ciliate cells containing a biogenous substance;

(ii) harvesting said culture medium containing the produced biomass at an extraction rate of about 0.1 to about 12 times said volume per day; and (iii) replacing the harvested culture medium containing the biomass with the same amount of complex axenic aqueous culture medium, so as to maintain a continuous fermentation culture.

2. The fermentation process as claimed in claim 1, wherein the ciliates belong to one of the taxonomic groups Holotricha, Peritricha, Spirotricha, Suctoria, Tetrahymena, Paramecium, Colpoda, Glaucoma, Parauronema, Engelmanniella, Stylonichia, Euplotes and Colpidium.

3. The fermentation process as claimed in claim 2, wherein the medium contains killed biomass of feed organisms for ciliates.

4. The fermentation process as claimed in claim 1, wherein the fermentation is carried out in a stirred, bubble column or airlift fermenter.

5. The fermentation process as claimed in claim 4, wherein the medium contains killed biomass of feed organisms for ciliates.

6. The fermentation process as claimed in claim 1, wherein the fermentation is carried out at a pH in the range from pH 4 to pH 9 and a fermentation temperature in the range from about 15 to about 40° C.

7. The fermentation process as claimed in claim 6, wherein the medium contains killed biomass of feed organisms for ciliates.

8. The fermentation process as claimed in claim 1, wherein the culture medium contains a carbon source which comprises one or more substances from the group consisting of: glucose, fructose, xylose, sucrose, maltose, starch, fucose, glucosamine, lactose, molasses, dextran, fatty acids, soya oil, sunflower oil, glycerol, glutamic acid, mannitol, skim-milk powder and acetate.

9. The fermentation process as claimed in claim 8, wherein the medium contains killed biomass of feed organisms for ciliates.

10. The fermentation process as claimed in claim 8, wherein the concentration of the carbon source is about 0.2 to about 20% by weight, based on the culture medium.

11. The fermentation process as claimed in claim 10, wherein the medium contains killed biomass of feed organisms for ciliates.

12. The fermentation process as claimed in claim 1, wherein the medium contains a nitrogen source which comprises one or more substances from the group consisting of: peptones, yeast extract, malt extract, meat extract, skim-milk powder, casamino acid, corn steep liquor, Na-glutamate, urea, ammonium acetate, ammonium sulfate, ammonium chloride and ammonium nitrate.

13. The fermentation process as claimed in claim 12, wherein tile medium contains killed biomass of feed organisms for ciliates.

14. The fermentation process as claimed in claim 12, wherein the concentration of the nitrogen source is about 0.1 to about 10% by weight, based on the culture medium.

15. The fermentation process as claimed in claim 14, wherein the medium contains killed biomass of feed organisms for ciliates.

16. The fermentation process as claimed in claim 1, wherein the medium contains at least one phosphate source selected from the group consisting of potassium phosphate and potassium dihydrogen phosphate.

17. The fermentation process as claimed in claim 16, wherein the medium contains killed biomass of feed organisms for ciliates.

18. The fermentation process as claimed in claim 1, wherein the medium contains one or more substances selected from the group consisting of ammonium sulfate, sodium sulfate, magnesium, iron, copper, calcium, vitamins, and trace elements.

19. The fermentation process as claimed in claim 18, wherein the medium contains killed biomass of feed organisms for ciliates.

20. The fermentation process as claimed in claim 1, wherein the medium contains killed biomass of feed organisms for ciliates.

21. The fermentation process as claimed in claim 1, wherein the produced biomass is separated off from the harvested culture medium by a method selected from the group consisting of centrifugation, tangential filtration, microfiltration, sedimentation and flotation.

22. The fermentation process as claimed in claim 1, additionally comprising the step of extracting from the produced biomass a biogenous substance selected from the group consisting of: peptides, proteins, enzymes, fatty acids, lipids, polysaccharides, nucleic acids, and secondary metabolites from the produced biomass.

* * * * *

UNITED STATES PATENT AND TRADEMARK OFFICE
CERTIFICATE OF CORRECTION

PATENT NO. : 6,716,617 B1
DATED : April 6, 2004
INVENTOR(S) : Thomas Kiy

It is certified that error appears in the above-identified patent and that said Letters Patent is hereby corrected as shown below:

Column 8,
Line 2, "skin-" should read -- skim --.
Line 7, "tile" should read -- the --.

Signed and Sealed this

Seventh Day of June, 2005

JON W. DUDAS
*Director of the United States Patent and Trademark Office*